(12) United States Patent
Onyemauwa et al.

(10) Patent No.: US 10,737,259 B2
(45) Date of Patent: Aug. 11, 2020

(54) SALT TOLERANT ANION EXCHANGE MEDIUM

(71) Applicant: Pall Corporation, Port Washington, NY (US)

(72) Inventors: Frank Onyemauwa, Pace, FL (US); Hassan Ait-Haddou, Gulf Breeze, FL (US)

(73) Assignee: Pall Corporation, Port Washington, NY (US)

( * ) Notice: Subject to any disclaimer, the term of this patent is extended or adjusted under 35 U.S.C. 154(b) by 85 days.

(21) Appl. No.: 16/119,557

(22) Filed: Aug. 31, 2018

(65) Prior Publication Data

US 2020/0070140 A1 Mar. 5, 2020

(51) Int. Cl.
  *B01J 41/13* (2017.01)
  *B01J 47/014* (2017.01)
  *B01J 41/04* (2017.01)
  *C07K 1/18* (2006.01)
  *C07K 16/06* (2006.01)

(52) U.S. Cl.
  CPC ............. *B01J 41/13* (2017.01); *B01J 41/04* (2013.01); *B01J 47/014* (2017.01); *C07K 1/18* (2013.01); *C07K 16/065* (2013.01)

(58) Field of Classification Search
  CPC .......... B01J 41/13; B01J 41/04; B01J 47/014; C07K 16/065; C07K 1/18
  USPC ....................................................... 521/27
  See application file for complete search history.

(56) References Cited

U.S. PATENT DOCUMENTS

| | | |
|---|---|---|
| 6,780,327 B1 | 8/2004 | Wu et al. |
| 6,783,937 B1 | 8/2004 | Hou et al. |
| 7,582,684 B2 | 9/2009 | Rasmussen et al. |
| 7,662,930 B2 | 2/2010 | Zhou |
| 8,114,611 B2 | 2/2012 | Bian et al. |
| 8,367,809 B2 | 2/2013 | Childs et al. |
| 8,658,702 B2 | 2/2014 | Diallo et al. |
| 8,673,988 B2 | 3/2014 | Graalfs et al. |
| 9,022,227 B2* | 5/2015 | Na .................... B01D 69/12 210/500.38 |
| 9,028,683 B2 | 5/2015 | Komiya et al. |
| 9,433,904 B2 | 9/2016 | Demmer et al. |
| 9,433,922 B2 | 9/2016 | Kozlov et al. |

(Continued)

FOREIGN PATENT DOCUMENTS

| | | |
|---|---|---|
| AU | 2011203555 A1 | 8/2011 |
| EP | 0347755 A2 | 12/1989 |

(Continued)

OTHER PUBLICATIONS

Intellectual Property Office of Singapore, Search Report in Application No. 10201907374S (dated Jun. 22, 2020).

*Primary Examiner* — Michael Bernshteyn
(74) *Attorney, Agent, or Firm* — Leydig, Voit & Mayer, Ltd.

(57) ABSTRACT

Disclosed is an anion exchange porous medium, e.g., a porous membrane, that includes a porous support and a crosslinked cationic polymer coating disposed thereon, wherein the cationic polymer of the crosslinked cationic polymer coating comprises polymerized monomer (A) and polymerized monomer (B) wherein A and B are as defined herein. Also disclosed are methods of preparing the anion exchange porous medium and of treating a fluid containing a biologic.

17 Claims, 8 Drawing Sheets

(56) References Cited

U.S. PATENT DOCUMENTS

| | | |
|---|---|---|
| 9,441,011 B2 | 9/2016 | Shinohara et al. |
| 9,725,545 B2 | 8/2017 | Wickert et al. |
| 9,758,547 B2 | 9/2017 | Rasmussen et al. |
| 2010/0323430 A1 | 12/2010 | Kozlov |
| 2011/0065900 A1 | 3/2011 | Johansson et al. |
| 2012/0121819 A1 | 5/2012 | Kozlov et al. |
| 2012/0168381 A1 | 7/2012 | Ramaswamy et al. |
| 2012/0292244 A1* | 11/2012 | Harrold ............... B01J 20/3293 210/263 |
| 2013/0090396 A1 | 4/2013 | MacDonald et al. |
| 2014/0238935 A1* | 8/2014 | Komkova .......... B01J 20/28033 210/635 |
| 2015/0344520 A1 | 12/2015 | Matsumoto et al. |
| 2019/0083943 A1 | 3/2019 | Hoshino et al. |

FOREIGN PATENT DOCUMENTS

| | | |
|---|---|---|
| EP | 1235748 | 5/2001 |
| EP | 1827691 | 4/2006 |
| EP | 2060316 A1 | 5/2009 |
| EP | 2386628 A1 | 11/2011 |
| EP | 2691772 | 10/2012 |
| EP | 2961762 | 9/2014 |
| EP | 3116645 | 9/2015 |
| WO | WO 2014/134147 A1 | 9/2014 |
| WO | WO 2017/029601 A1 | 2/2017 |
| WO | WO 2017/146231 A1 | 8/2017 |
| WO | WO 2017/205722 A1 | 11/2017 |
| WO | WO-2017205722 A1 * | 11/2017 ............. B01D 71/82 |

\* cited by examiner

SALT TOLERANT ANION EXCHANGE MEDIUM

BACKGROUND OF THE INVENTION

Production of monoclonal antibody (mAb) and purification thereof continue to pose a problem due to the high cost of the process. Contributing to the high cost are the several purification steps the biomolecules need to go through during isolation. For example, one of the purification steps is protein A affinity chromatography, wherein Staphylococcal protein A binds IgG molecules of subclasses 1, 2, and 4 with high selectivity and minimal interaction with the Fab region, the active region of the drug molecule. With the biotechnology market rapidly growing, improvements in these purification steps are becoming more desirable and more valuable in bringing biologics to the market in a timely space and at reduced cost.

During protein purification, polishing steps using anion exchanger media require that the media are not only selective to impurities but also tolerate feedstocks with high salt conductivities, for example, up to 15 mS/cm or more.

The foregoing shows that there exists an unmet need for anion exchanger media that are not only selective to impurities but also tolerate feedstocks with high salt conductivities.

BRIEF SUMMARY OF THE INVENTION

The present invention provides anion exchange media, e.g., anion exchange porous media, e.g., beads, fibers, and membranes, comprising ion exchange polymers. The anion exchange media have salt tolerant properties and high dynamic binding capacities (DBC) for proteins, e.g., a DBC for bovine serum albumin (BSA) of up to 300 mg/mL at 10 CV/min flow rate.

DETAILED DESCRIPTION OF THE INVENTION

Figure 1:
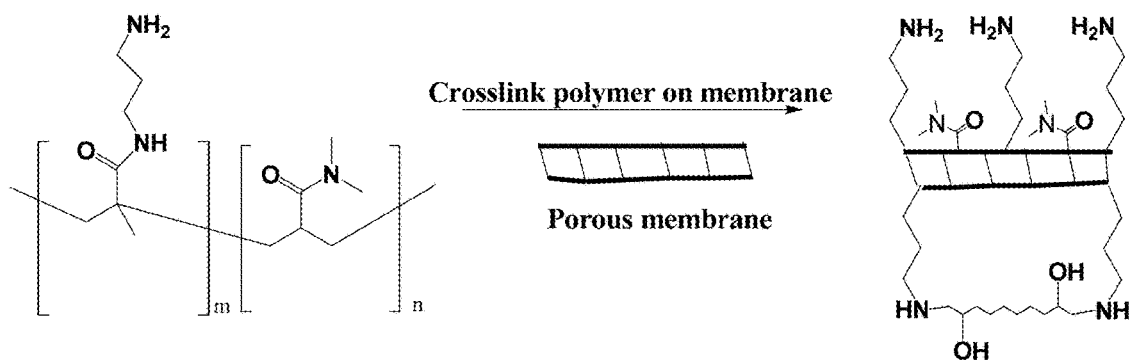
FIG. 1 schematically depicts the preparation of a porous medium according to an embodiment of the invention.
Figure 2:
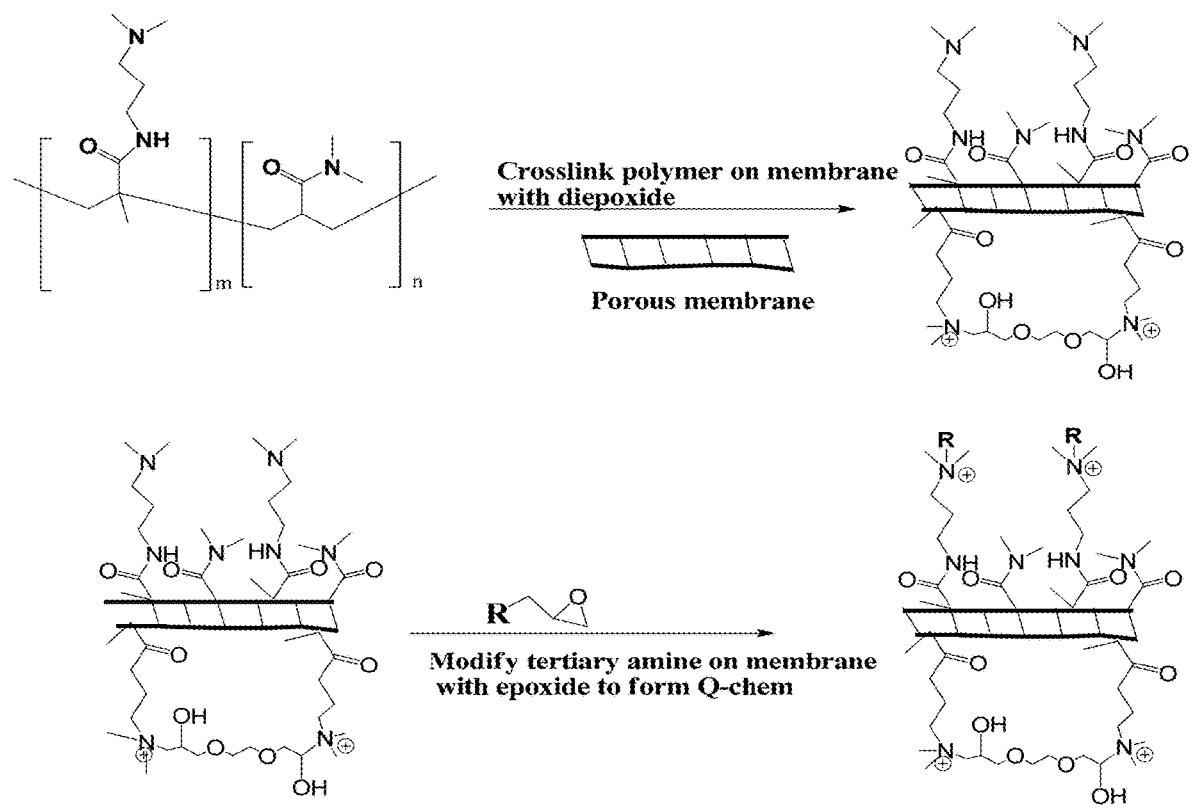
FIG. 2 depicts schematically depicts the preparation of a porous medium according to another embodiment of the invention.
Figure 3:
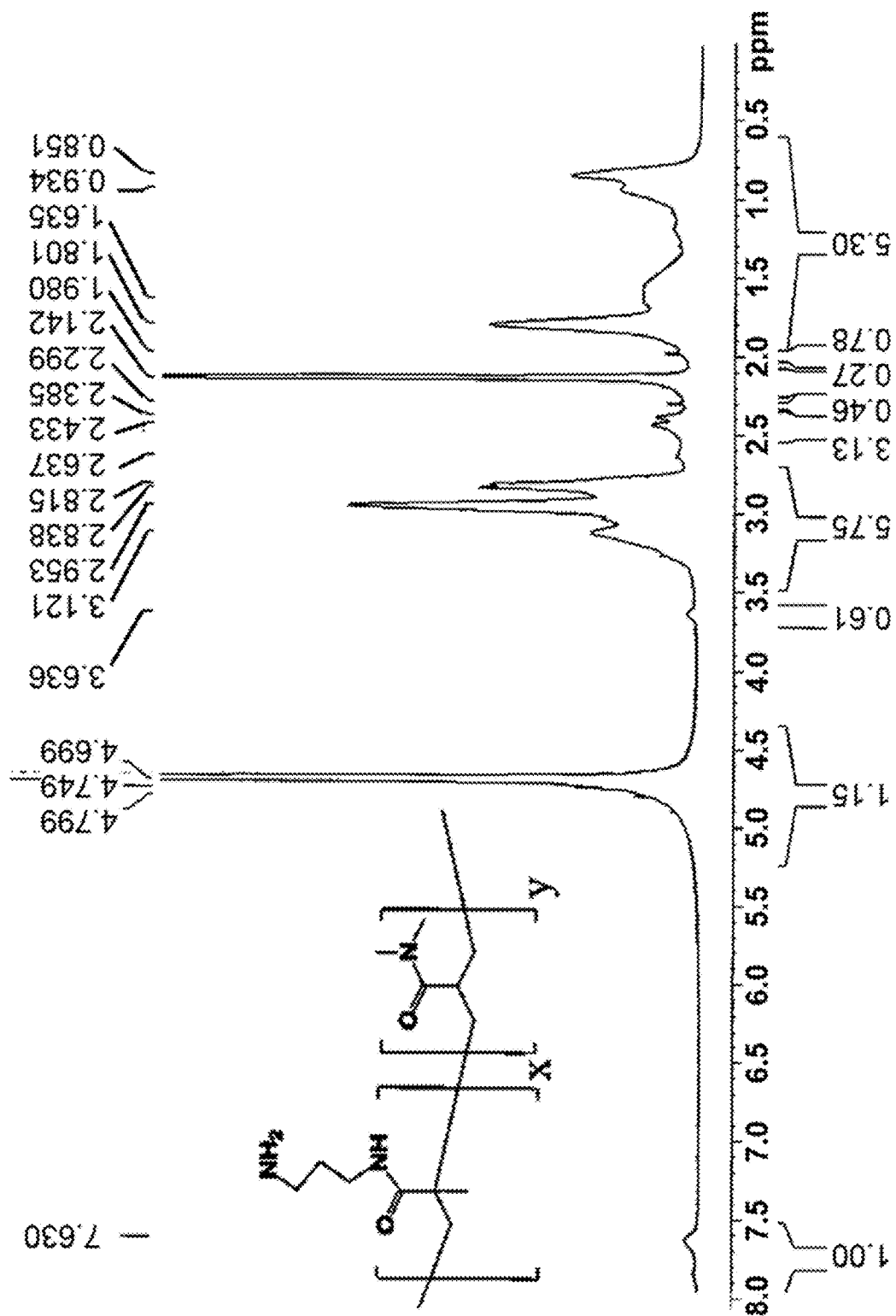
FIG. 3 depicts the NMR spectrum of poly(N-3-aminopropylmethacrylamide-co-dimethylacrylamide).
Figure 4:
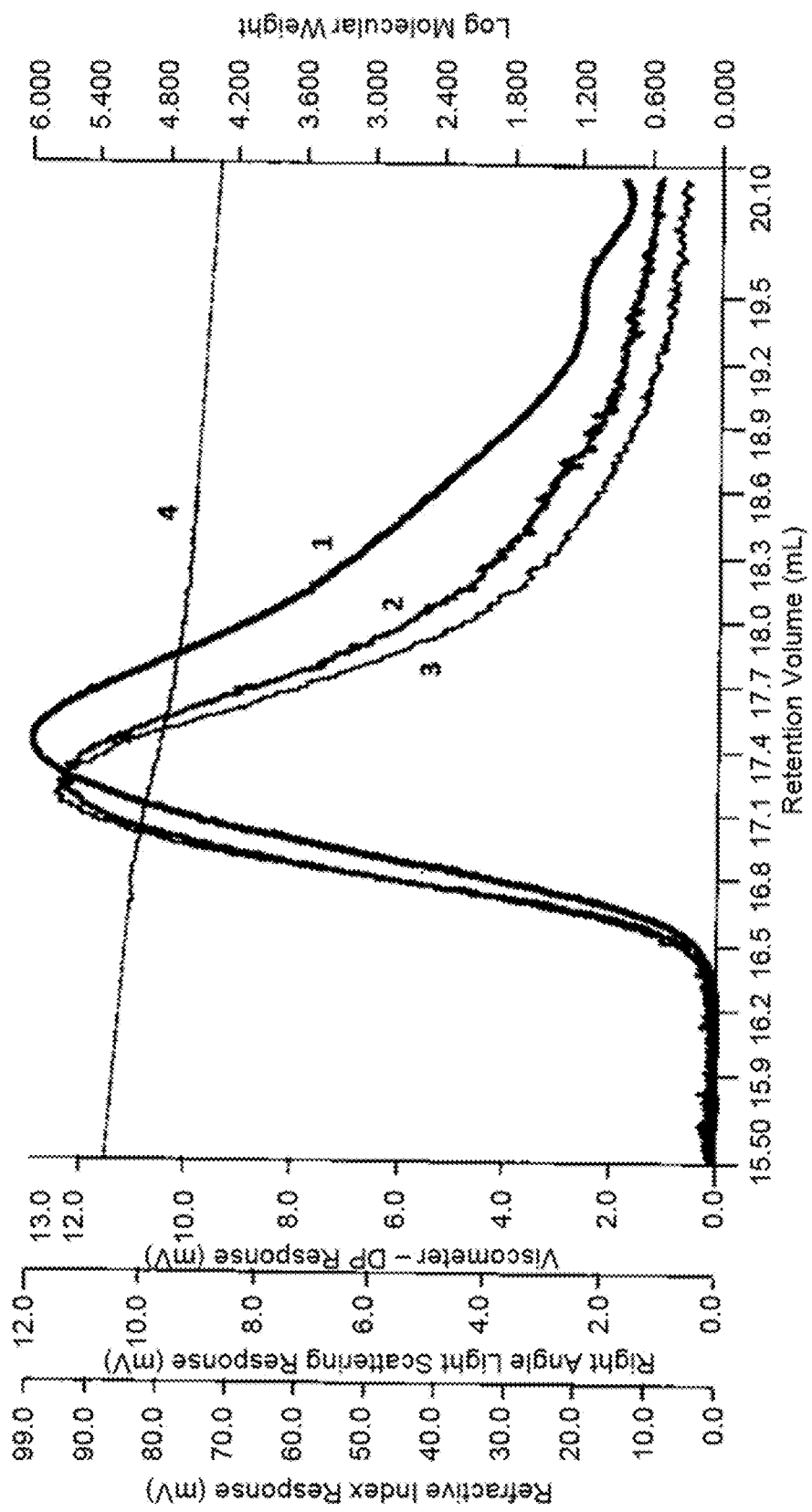
FIG. 4 depicts the triple detection elution profile obtained from the injection of a poly(N-3-aminopropylmethacrylamide-co-N,N-dimethylacrylamide) sample in accordance with an embodiment of the invention, wherein 1 represents the refractive index (RI), 2 represents the viscosity, 3 represents the relative angle laser light scattering (RALS) data, and 4 represents log MW.
Figure 5:
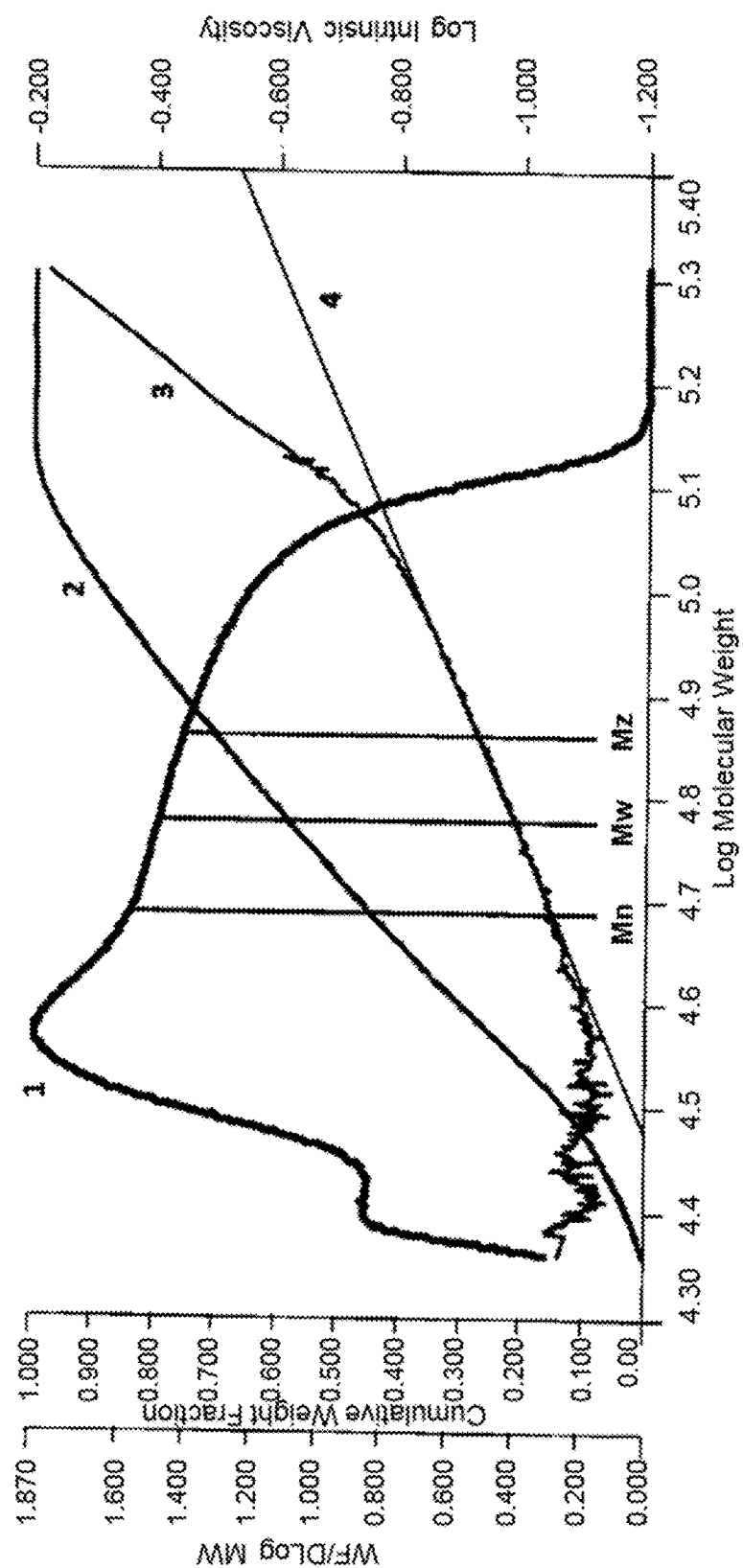
FIG. 5 depicts an overlay of the MW distribution plots obtained from the injection of a poly(N-3-aminopropylmethacrylamide-co-N,N-dimethylacrylamide) sample in accordance with an embodiment of the invention, wherein 1 represents the Normalized Weight Fraction (WF/d log MW), 2 represents Cumulative Weight Fraction, and 3 represents the Mark-Houwink-Sakurada plot ($\log([r])$ vs $\log(M)$).
Figure 6:
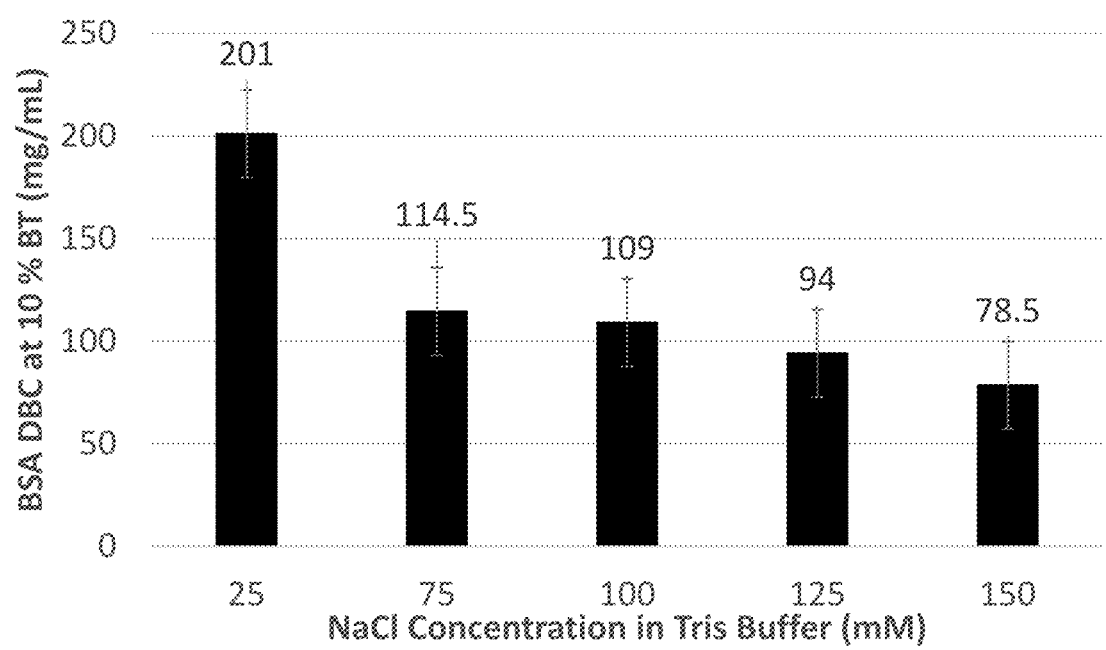
FIG. 6 depicts the BSA 10% breakthrough DBC of a porous medium made from poly(N-3-aminopropylmethacrylamide-co-N,N-dimethylacrylamide) and crosslinked to contain primary amino groups, in accordance with an embodiment of Example 1 of the invention, at different salt concentrations.
Figure 7:
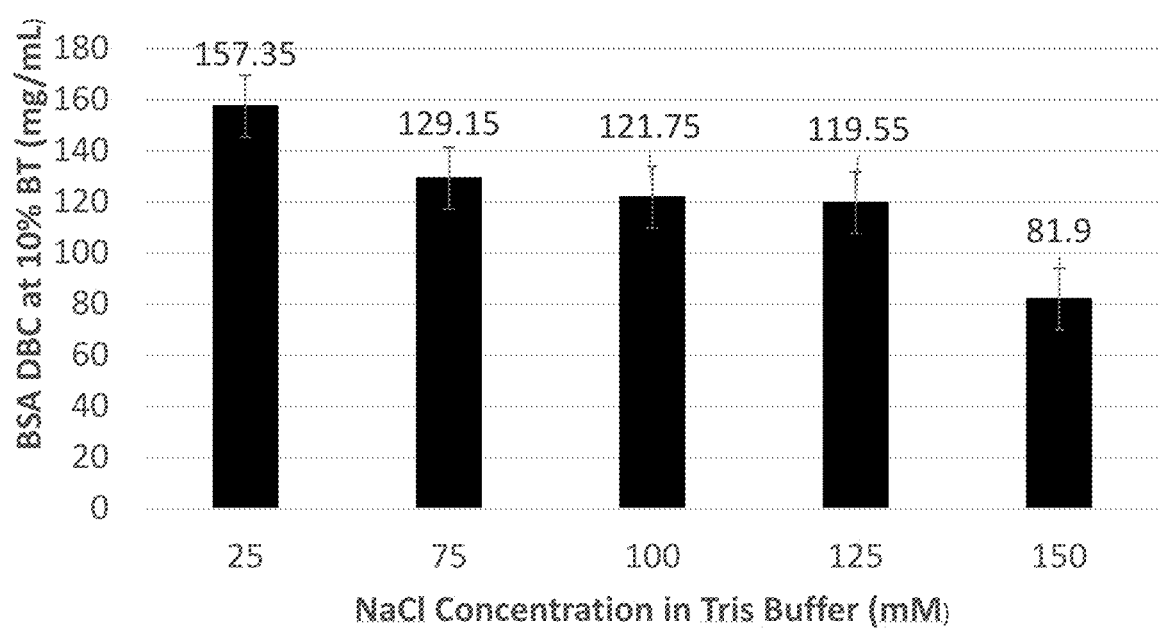
FIG. 7 depicts the BSA 10% breakthrough DBC of a porous medium made from Poly(dimethylaminopropylacrylamide-co-dimethylacrylamide) and crosslinked to contain tertiary amine groups, and subsequently quaternized with phenyl glycidyl ether in accordance with another embodiment in Examples 8 and 9 of the invention at different salt concentrations.
Figure 8:
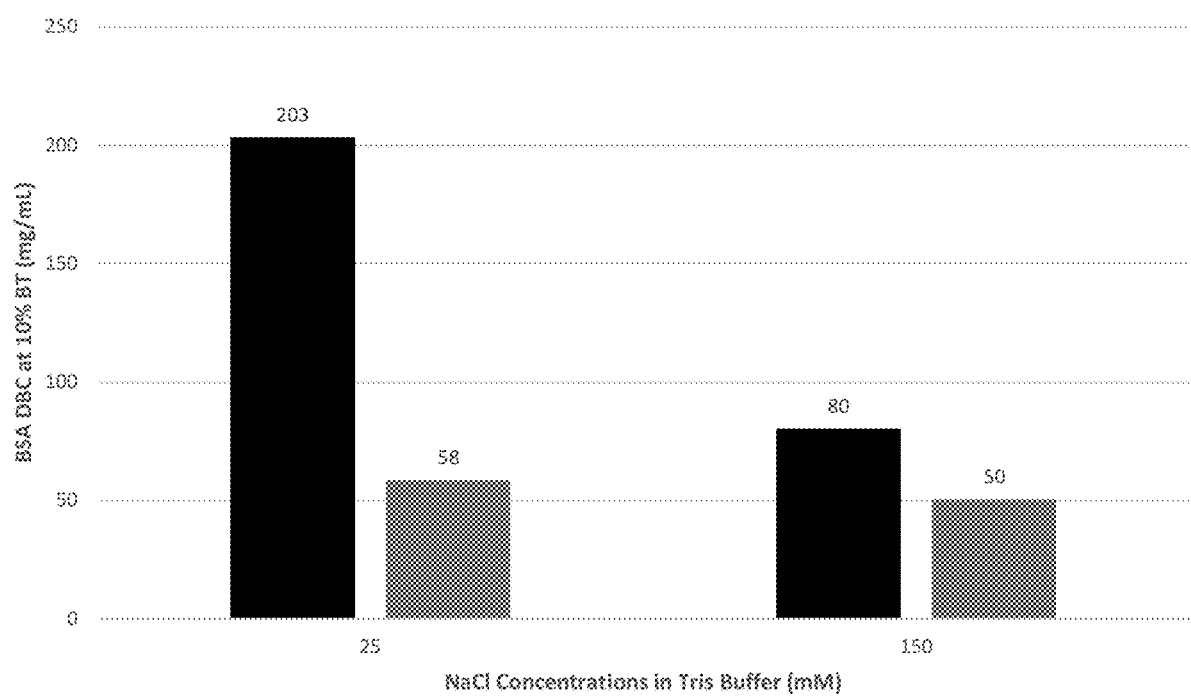
FIG. 8 depicts the BSA 10% breakthrough DBC of the medium illustrated in FIG. 6 (solid black bars) vs. the breakthrough performance of a Sartobind STIC PA membrane (grey bars).
Figure 9:
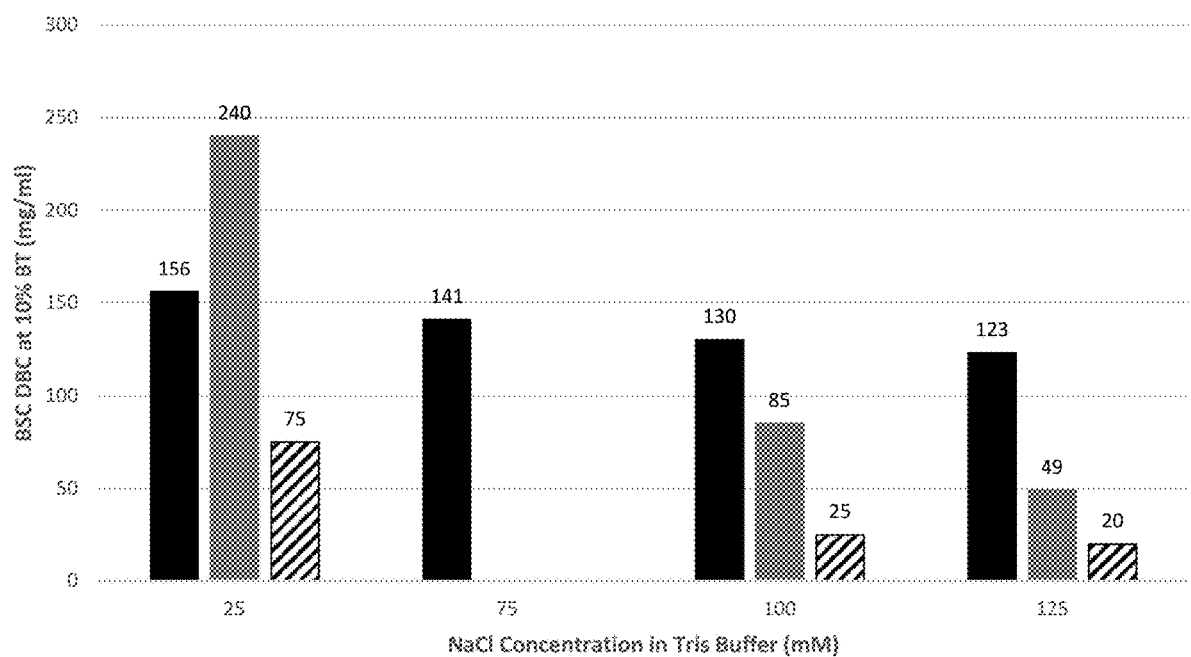
FIG. 9 depicts the BSA 10% breakthrough DBC of a medium in accordance with an embodiment of the invention of Examples 8 and 9 (solid black bars) vs. commercially available NatriFlo HD-Q membranes (grey bars and hatched bars).

The present invention provides an anion exchange porous medium, e.g., a membrane, comprising a porous support and a crosslinked cationic polymer coating disposed thereon, wherein the cationic polymer of the crosslinked cationic polymer coating comprises polymerized monomer (A) and polymerized monomer (B), wherein monomer (A) has the formula:

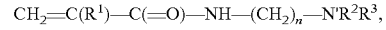

wherein n is 1-6, and monomer (B) has the formula:

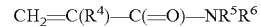

wherein $R^1$ and $R^4$ are independently H or $C_1$-$C_6$ alkyl, and $R^2$, $R^3$, $R^5$, and $R^6$ are independently H, $C_1$-$C_6$ alkyl, $C_6$-$C_{10}$ aryl, $C_1$-$C$ alkoxy $C_1$-$C$ alkyl, or triphenylmethyl.

In an embodiment, the porous medium is a bead or fiber or porous membrane.

In an embodiment of the medium, $R^1$ is $C_1$-$C_6$ alkyl, and $R^4$ is H.

The $C_1$-$C_6$ alkyl group throughout this application can have 1, 2, 3, 4, 5, or 6 carbon atoms; the alkyl group can be linear or branched. Examples of alkyl groups include methyl, ethyl, n-propyl, i-propyl, n-butyl, i-butyl, t-butyl, n-pentyl, 2-methylbutyl, n-hexyl, 2-methylpentyl, and 3-methylpentyl.

In an embodiment of the invention, $R^1$ is methyl.

In any of the embodiments above, $R^2$ and $R^3$ are H, and $R^5$ and $R^6$ are independently $C_1$-$C_6$ alkyl.

In any of the embodiments above, $R^2$ and $R^3$ are H, and $R^5$ and $R^6$ are methyl.

In any of the embodiments above, $R^2$, $R^3$, $R^5$, and $R^6$ are independently H, methyl, phenyl, methoxy methyl, or triphenylmethyl.

In any of the embodiments above, $R^2$ and $R^3$ are H, and $R^5$ and $R^6$ are independently methyl, phenyl, methoxy methyl, or triphenylmethyl.

In an embodiment, the crosslinked cationic polymer comprises two different polymerized monomers (A) and one polymerized monomer (B).

In an embodiment, the crosslinked cationic polymer comprises two different polymerized monomers (A) and two different polymerized monomers (B).

In an embodiment, the crosslinked cationic polymer comprises one polymerized monomer (A) and two different polymerized monomers (B).

Examples of combinations of monomers constituting the polymer include the following:

N-(3-aminopropyl)methacrylamide and acrylamide,
N-(3-aminopropyl)methacrylamide and N-isopropylacrylamide,
N-(3-aminopropyl)methacrylamide and tertbutylacrylamide,
N-(3-aminopropyl)methacrylamide and ethylacrylamide,
N-(3-aminopropyl)methacrylamide and phenylacrylamide,
N-(3-aminopropyl)methacrylamide and N,N-diethyl acrylamide,
N-(3-aminopropyl)methacrylamide and N-(isobutoxymethyl)acrylamide,
N-(3-aminopropyl)methacrylamide and N-(triphenylmethyl)acrylamide,
N-(3-aminopropyl)methacrylamide and N,N-dimethylacrylamide,
N-(2-aminoethyl)methacrylamide and N-isopropylacrylamide,
N-(2-aminoethyl)methacrylamide and tertbutyl acrylamide,
N-(2-aminoethyl)methacrylamide and phenylacrylamide,
N-(2-aminoethyl)methacrylamide and N,N-diethyl acrylamide,
N-(2-aminoethyl)methacrylamide and ethyl acrylamide,
N-(2-aminoethyl)methacrylamide and N-(isobutoxymethyl) methacrylamide,
N-(2-aminoethyl)methacrylamide and N-(triphenylmethyl) acrylamide, and
N-(2-aminoethyl)methacrylamide and N,N-dimethylacrylamide.

The invention provides, in embodiments, one or more of the following polymers:

A copolymer comprising N-(3-aminopropyl)methacrylamide and N-dimethylacrylamide and crosslinked on a membrane using the primary amine moiety of the copolymer.

A copolymer comprising N-(3-aminopropyl)methacrylamide and N-dimethylacrylamide and coupled to a membrane, e.g., cellulose beads, agarose beads or fibrous medium using the primary amine moiety of the copolymer, wherein any of the medium can be porous or non-porous.

A copolymer comprising an amino alkyl methacrylamide and N-dimethylacrylamide and crosslinked on a membrane using the primary amine moiety of the copolymer.

A terpolymer comprising a N-(3-aminopropyl)methacrylamide, N-dimethyl acrylamide and an alkylacrylamide, e.g., N-tert-butyl acrylamide, N-phenylacrylamide, N,N-diethylacrylamide, N-isopropylacrylamide, N-ethylacrylamide, N,N-diethylmethacrylamide, N-(isobutoxymethyl)methacrylamide, and N-(triphenylmethyl)methacrylamide, and crosslinked on a membrane using the primary amine moiety of the copolymer.

A terpolymer comprising N-(3-aminopropyl)methacrylamide, N-dimethyl acrylamide and an alkylacrylamide e.g., N-tert-butyl acrylamide, N-phenylacrylamide, N-diethylacrylamide, N-isopropylacrylamide, N-ethylacrylamide, N,N-diethylmethacrylamide, N-(isobutoxymethyl)methacrylamide, and N-(triphenylmethyl) methacrylamide, and crosslinked on a membrane using a tertiary and primary amine moiety on the terpolymer.

The present invention provides a salt-tolerant, anion-exchange porous medium, e.g., porous membrane, that advantageously can be used for, e.g., polishing of antibodies, BSA clearance, host cell proteins (HCP) clearance, DNA clearance, and viral vector purification.

The present invention provides a salt-tolerant, anion-exchange porous medium, e.g., membrane, where the salt tolerant properties of the co or terpolymer coated on the porous support are advantageously imparted by aminoalkyl acrylamide portion of the polymer.

The present invention provides a copolymer comprising N-(3-Aminopropyl)methacrylamide and N,N-dimethylacrylamide.

The present invention provides a copolymer of N-[3-(dimethylamino)propyl]methacrylamide and N,N-dimethylacrylamide crosslinked on a medium through the tertiary amine moiety.

The present invention provides a copolymer of N-[3-(dimethylamino)propyl]methacrylamide and N,N-dimethylacrylamide partially cross-linked on a medium through the tertiary amine moieties to form quaternary ammonium groups.

The present invention provides a porous medium coated with a copolymer of N-[3-(dimethylamino)propyl]methacrylamide and N,N-dimethylacrylamide.

The present invention provides a porous medium coated with a copolymer of N-[3-(dimethylamino)propyl]methacrylamide and N,N-dimethylacrylamide, and further quaternized with any of the following epoxides: isopropyl glycidyl ether, phenyl glycidyl ether, tert-butyl glycidyl ether, ethylhexyl glycidyl ether, glycidyl methyl ether, benzyl glycidyl ether, alkane epoxide, or aromatic epoxides.

The molecular weight of the copolymers can be of any suitable range, for example, from 10 to 500 kD, 10 to 300 kD, 10 to 100 kD, or 20 to 100 kD, and preferably from 20 kD to 50 kD, wherein the molecular weight is as determined by triple detection GPC.

Comonomers A and B can be in any suitable molar ratios, e.g., 1 to 10 to 10:1, 1:5 to 5:1, or 1:3 to 3:1, respectively. For example, when comonomers A and B, in particular N-(3-aminopropyl)methacrylamide and N-dimethylacrylamide, are used to form a polymer crosslinked on a membrane, ranges of monomer combination, in particular for improving salt tolerance in chromatographic application, are from mole ratios of 1:5 to mole ratios of 5:1 N-(3-aminopropyl)methacrylamide:N-dimethylacrylamide. When comonomers of any amino alkyl methacrylamide and N-dimethylacrylamide are used to form a polymer cross-linked on a membrane, ranges of monomer combination that impact salt tolerance in chromatographic application include mole ratios of 1:5 to mole ratios of 5:1 N-(3-aminopropyl) methacrylamide:N-dimethylacrylamide.

When ter-monomers comprising N-(3-aminopropyl) methacrylamide, N-dimethyl acrylamide, and any alkylacrylamide e.g., N-tert-butyl acrylamide, N-phenylacrylamide, N-diethylacrylamide, N-isopropylacrylamide, N-ethylacrylamide, N-diethylmethacrylamide, N-(isobutoxymethyl) methacrylamide, and N-(triphenylmethyl)methacrylamide, are used to form a crosslinked coating on a membrane, ranges of monomer combination that impact salt tolerance in chromatographic application while still permitting efficient recovery of the protein are from mole ratios of 1:4.75:0.25 to mole ratios of 2:1:1.

When a copolymer of N-(3-aminopropyl)methacrylamide and N,N-dimethylacrylamide is used to form a polymer crosslinked on a membrane for protein purification, ranges of polymer concentrations that impart high salt tolerance while simultaneously providing high dynamic binding capacities up to 300 mg/mL BSA are from 1%-10%.

In embodiments, the ratios of copolymers of N-[3-(dimethylamino)propyl]methacrylamide and N,N-dimethylacrylamide that result in optimum gel network are 5:1 to 1:5.

The present invention further provides a method for producing a salt tolerant positively charged medium (e.g., a porous membrane) comprising:
(i) polymerizing a monomer mixture comprising at least one monomer (A) and at least one monomer (B) to obtain a copolymer,
wherein monomer (A) has the formula:

$$CH_2=C(R^1)-C(=O)-NH-(CH_2)_n-NR^2R^3$$

wherein n is 1-6, and monomer (B) has the formula:

$$CH_2=C(R^4)-C(=O)-NR^5R^6$$

wherein $R^1$ and $R^4$ are independently H or $C_1$-$C_6$ alkyl, and
$R^2$, $R^3$, $R^5$, and $R^6$ are independently H, $C_1$-$C_6$ alkyl, $C_6$-$C_{10}$ aryl, $C_1$-$C$ alkoxy $C_1$-$C$ alkyl, or triphenylmethyl;
(ii) coating a solution of the copolymer obtained in (i) and a crosslinking agent on a porous support to obtain a crosslinked copolymer coating on the porous support; and
(iii) quaternizing at least a portion of the amino groups present on the copolymer coating obtained in (iii) by reacting with a quaternizing agent.

Polymerization of the monomers can be carried out using suitable initiators—free radical, cationic, or anionic initiators, and in particular with free radical initiators, for example, thermally activated free radical initiators such as azo compounds, persulfates, peroxides, peracids, peracetates, and organometallics. Examples of free radical initiators include AIBN, 4,4-azobis(4-cyanovaleric acid), 1,1'-azobis(cyclohexanecarbonitrile), benzoyl peroxide, 2,2-bis(tert-butylperoxy)butane, 1,1-bis(tert-butylperoxy)cyclohexane, dicumylperoxide, tert-butyl peroxybenzoate, tert-amyl peroxybenzoate, and potassium persulfate.

In accordance with embodiments, the coating solution can be spin coated on a porous support medium, e.g., porous support membrane, drip coated on a porous membrane, spray coated on a porous support membrane, slot die coating or dip coated on a porous support membrane.

Preferred embodiments of the polymers include poly(dimethylacrylamide-co-polyacrylamidopropylamine), poly(acrylamide-co-polyacrylamidopropylamine), poly(dimethyl acrylamide-co-aminopropyl methacrylamide), N,N-dimethyl acrylamide, N-(3-aminopropyl)methacrylamide, N-[3-(dimethylamino)propyl]methacrylamide, cationic propylacrylamide, and poly(aminopropyl methacrylamide).

In an embodiment of the above method, the crosslinking agent is a polyfunctional agent, that is, it comprises two, three, or more groups selected from epoxide, aldehyde, halide, and ester; for example, the crosslinking agent is selected from ethylene glycol diglycidyl ether, propylene glycol diglycidyl ether, glyceryl triglycidyl ether, polyethylene glycol diglycidyl ether, glycol di- or poly-mesylate ester, e.g., ethylene glycol dimesylate ester, propylene glycol dimesylate ester, and glycerol trimesylate ester, glycol di- or tritosylate ester, e.g., ethylene glycol ditosylate ester, propylene glycol ditosylate ester, and glycerol tritosylate ester, glycol di- or tri-chlorides, e.g., ethylene glycol dichloride, propylene glycol dichloride, and glycerol trichloride, and any combination thereof.

The present invention provides, in embodiments, N-(3-aminopropyl)methacrylamide, N-[3-(dimethylamino)propyl]methacrylamide, N-dimethyl acrylamide, poly(N,N-dimethyl acrylamide-co-aminopropyl methacrylamide), poly(N,N-dimethyl acrylamide-co-aminopropyl methacrylamide), poly(N,N-dimethylaminopropylacrylamide-co-N,N-dimethylacrylamide) coated and crosslinked with diepoxides on porous high density polyethylene membranes, polyether sulfone membranes, polyvinylidene fluoride membrane, polytetrafluoroethylene membrane, polyphenylsulfone membrane, polyphenylene sulfide membrane, polyethylene and polypropylene membranes, polyester membranes, melt blown polyester membranes, melt blown polypropylene membranes, cellulose membranes, nylon membranes, and polyvinylchloride/acrylonitrile.

The present invention further provides a method of treating a fluid containing a desired protein and one or more negatively charged species, the method comprising contacting the fluid with the positively charged medium or membrane as described above and recovering the desired protein with a reduced concentration of one or more of the negatively charged species.

Prolonged exposure of the anion exchanger membrane to high temperatures should be avoided, e.g. temperatures >80° C. for longer than 20 minutes after coating.

In an embodiment, the fluid treated above has a salt content such that the fluid exhibits an electrical conductivity of up to 30 mS/cm or higher The invention has advantages of high dynamic binding capacities at salt concentrations up to 150 mmol sodium chloride, high water flow rate up to 200 LMH, high stability to 1 M NaOH, and can be recycled up to 50 times with 1 M NaOH wash.

In an embodiment of the above method, the desired protein is a monoclonal antibody. In a further embodiment of the method, the desired protein is a biologic.

A preferred use of the invention is for polishing steps in mAb and viral vector purification, and for trace metal removal from Micro E solvents.

In accordance with an embodiment of the invention, the porous membrane can be a nanoporous membrane, for example, a membrane having pores of diameter between 1 nm and 100 nm, or a microporous membrane, for example, a membrane having pores of diameter from 0.2 μm to 10 μm.

The porous support on which the coating is provided can be of any suitable material, e.g., a polymer, metallic, or ceramic, and in particular a polymer, for example, cellulosic polymers such as cellulose esters, e.g., cellulose acetate and cellulose propionate, and cellulose mixed esters such as cellulose acetate/propionate, polysulfone (PSU), polyethersulfone (PES), polyphenyl ether (PPE), polyphenylene ether sulfone (PPES), polyphenylene oxide (PPO), polycarbonate (PC), poly(phthalazinone ether sulfone ketone) (PPESK), polyether ether ketone (PEEK), polyether ketone ketone (PEKK), polyetherimide (PEI) and blends thereof. The porous support can be a flat sheet, hollow fiber, filament, bead—hollow or non-hollow, felt pad, woven or non-woven matrix, or any suitable combination thereof.

The porous medium according to embodiments of the invention can be disposed in a housing comprising at least one inlet and at least one outlet and defining at least one fluid flow path between the inlet and the outlet, wherein at least one inventive membrane or a filter including at least one inventive membrane is across the fluid flow path, to provide a filter device or filter module. In an embodiment, a filter device is provided comprising a housing comprising an inlet and a first outlet, and defining a first fluid flow path between the inlet and the first outlet; and at least one inventive membrane or a filter comprising at least one inventive membrane, the inventive membrane or filter comprising at least one inventive membrane being disposed in the housing across the first fluid flow path.

For crossflow applications, in an embodiment, at least one inventive porous membrane or filter comprising at least one inventive membrane is disposed in a housing comprising at least one inlet and at least two outlets and defining at least a first fluid flow path between the inlet and the first outlet, and a second fluid flow path between the inlet and the second outlet, wherein the inventive membrane or filter comprising at least one inventive membrane is across the first fluid flow path, to provide a filter device or filter module. In an illustrative embodiment, the filter device comprises a crossflow filter module, the housing comprising an inlet, a first outlet comprising a concentrate outlet, and a second outlet comprising a permeate outlet, and defining a first fluid flow path between the inlet and the first outlet, and a second fluid flow path between the inlet and the second outlet, wherein at least one inventive membrane or filter comprising at least one inventive membrane is disposed across the first fluid flow path.

The filter device or module may be sterilizable. Any housing of suitable shape and providing an inlet and one or more outlets may be employed.

The housing can be fabricated from any suitable rigid impervious material, including any impervious thermoplastic material, which is compatible with the fluid being processed. For example, the housing can be fabricated from a metal, such as stainless steel, or from a polymer, e.g., transparent or translucent polymer, such as an acrylic, polypropylene, polystyrene, or a polycarbonate resin.

The following examples further illustrate the invention but, of course, should not be construed as in any way limiting its scope.

Example 1

This example illustrates the preparation of a porous membrane in accordance with an embodiment of the invention.

N-(3-aminopropyl)methacrylamide hydrochloride (17.9 g, 100 mM) was mixed with N,N-dimethylacrylamide (4.96 g, 50 mM) in DI water (210 g), degassed for 5 minutes, followed by the addition of ammonium persulfate (0.514 g, 2.25 mmol) to obtain a solution. Polymerization was initiated by raising the temperature of the solution to 60° C. and kept for 2 hours at this temperature. The polymerization mixture was cooled to room temperature, and stored at 5-8° C.

A 5.5% polymer coating solution was prepared from the 10% stock polymer solution with 0.85% surfactant and 0.45% of a crosslinking agent. The pH of the solution was adjusted to 10, and a 3 micron HDPE porous membrane was dip-coated with the solution. The coated membrane was crosslinked at room temperature overnight.

Example 2

This example illustrates the preparation of the copolymer, poly(N-3-aminopropyl)methacrylamide-co-N,N-dimethylacrylamide, (PAPMA-DMAM), in accordance with an embodiment of the invention.

N-(3-aminopropyl)methacrylamide hydrochloride (17.9 g, 100 mM) was mixed with N,N-dimethylacrylamide (9.92 g, 100 mM) in DI water, and degassed for 5 minutes, followed by the addition of ammonium persulfate (0.514 g, 2.2 mmol). The reaction mixture was stirred at 60° C. for 2 hours and allowed to cool to room temperature, and the copolymer was isolated from the reaction mixture by precipitation in isopropanol

Example 3

This example illustrates the preparation of a terpolymer, poly(3-aminopropyl acrylamide-co-dimethylacrylamide-co-t-butylacrylamide), in accordance with an embodiment of the invention.

N-(3-aminopropyl)methacrylamide hydrochloride (12 g, 67 mM) was mixed with N,N-dimethylacrylamide (6.7 g, 67 mM), N-tert-butylacrylamide (2 g, 15.7 mM in IPA 8 g) and DI water 170 g), degassed for 5 minutes, followed by the addition of ammonium persulfate (0.546 g, 1.6 mM). The reaction mixture was stirred at 60° C. for 2 hours and allowed to cool to room temperature.

Example 4

This example illustrates the preparation of a terpolymer, poly(aminopropyl acrylamide-co-acrylamide-co-t-butylacrylamide), in accordance with an embodiment of the invention.

N-(3-aminopropyl)methacrylamide hydrochloride (12 g, 67 mM) was mixed with acrylamide (2.4 g, 33 mM), N-tert-butylacrylamide (4.27 g, 33.6 mM in IPA 15.73 g), and di-water 264 g), degassed for 5 minutes, followed by the addition of ammonium persulfate (0.546 g, 1.6 mM). The reaction mixture was stirred at 60° C. for 2.5 hours and allowed to cool to room temperature.

Example 5

This example illustrates the preparation of a terpolymer, poly(aminopropyl acrylamide-co-isopropylacrylamide-co-t-butylacrylamide), in accordance with an embodiment of the invention.

N-(3-aminopropyl)methacrylamide hydrochloride (12 g, 67 mM) was mixed with N-isopropylacrylamide (3.79 g, 33.6 mM), N-tert-butylacrylamide (4.27 g, 33.6 mM in IPA 15.73 g), and DI water (284 g), degassed for 5 minutes, followed by the addition of ammonium persulfate (0.445 g, 1.6 mM). The reaction mixture was stirred at 60° C. for 2.5 hours and allowed to cool to room temperature.

Example 6

This example illustrates the preparation of a copolymer, poly(N-3-aminopropyl acrylamide-co-acrylamide) (at 10% concentration), in accordance with an embodiment of the invention.

Acrylamide (10 g, 140.7 mM) was mixed with N-(3-aminopropyl)methacrylamide (12.6 g, 70.3 mM) and di-water (209.7 g), degassed for 5 minutes, followed by addition of ammonium persulfate (722 mg, 3 mM). The reaction mixture was stirred at 60° C. for 2.5 hours and allowed to cool to room temperature.

Example 7

This example illustrates the preparation of an anion exchanger—quaternary ammonium acrylamide copolymer, poly(N,N-dimethylaminopropyl acrylamide-co-dimethylacrylamide), (PDMAPA-DMA), in accordance with an embodiment of the invention.

N-[3-(dimethylamino)propyl]methacrylamide (17.18 g, 100.9 mM) and N,N-dimethylacrylamide (20 g, 201.8 mM) was mixed with di-water (334.6 g), and degassed for 10 minutes, followed by the addition of ammonium persulfate (1.04 g, 4.5 mM, 1.5 mol %). Degassing was continued for additional 10 minutes, and the mixture was polymerized at 60° C. for 2.5 hours.

Example 8

This example illustrates the preparation of a coating in accordance with an embodiment of the invention, which involves a 5% DMAPAM-DMAM coating (100 g mix).

10% PDMAPA-DMA (50 g) was mixed with water (49 g), polyethylene glycol diglycidyl ether (150 mg), and Triton X-100 (850 mg). The pH of coating solution was adjusted to pH of 10. A 3 μm HDPE membrane was coated with the coating solution by dip coating. The coated membrane was sandwiched between two pipettes and scraped from top to bottom to provide a coating of uniform thickness. The membrane was either allowed to crosslink at 65° C. for one hour, or at room temperature overnight. The resulting membrane was leached in cold water for 4-24 hours and allowed to dry.

Quaternization: The 3 μm HDPE membrane with 5% DMAPA-DMA coating was added to containers, each containing 10% of one of the following quaternizing reagents: isopropyl glycidyl ether, phenyl glycidyl ether, tert-butyl glycidyl ether, ethylhexyl glycidyl ether, glycidyl methyl ether, or benzyl glycidyl ether, by weight and a mixture of water and isopropanol (IPA) 50:50 by weight. The pH of mixture was adjusted to between 10 and 11, preferably pH 10.5. The mixture was tumbled at room temperature for 48 hours. The resulting membrane was cleaned with water and IPA to remove excess the epoxy ether. The membrane was dried at room temperature overnight or at 60° C. for one hour.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An anion exchange porous medium comprising a porous support and a crosslinked cationic polymer coating disposed thereon, wherein the cationic polymer of the crosslinked cationic polymer coating comprises a polymer comprising at least one polymerized monomer (A), at least one polymerized monomer (B), and at least one polymerized crosslinking agent, wherein said polymer has been quaternized with a quaternizing agent, wherein monomer (A) has the formula:

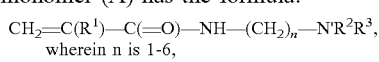
wherein n is 1-6, monomer (B) has the formula:

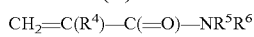

wherein the crosslinking agent is an agent having two, three, or more epoxy groups, and the quaternizing agent is a monoglycidyl ether, wherein $R^1$ and $R^4$ are independently H or $C_1$-$C_6$ alkyl, and $R^2$, $R^3$, $R^5$, and $R^6$ are independently H, $C_1$-$C_6$ alkyl, $C_6$-$C_{10}$ aryl, $C_1$-C alkoxy $C_1$-C alkyl, or triphenylmethyl.

2. The anion exchange porous medium of claim 1, wherein $R^1$ is $C_1$-$C_6$ alkyl and $R^4$ is H.

3. The anion exchange porous medium of claim 1, wherein $R^1$ is methyl.

4. The anion exchange porous medium of claim 1, wherein $R^2$ and $R^3$ are H, and $R^5$ and $R^6$ are independently $C_1$-$C_6$ alkyl.

5. The anion exchange porous medium of claim 1, wherein $R^2$ and $R^3$ are H, and $R^5$ and $R^6$ are methyl.

6. The anion exchange porous medium of claim 1, wherein $R^2$, $R^3$, $R^5$, and $R^6$ are independently H, methyl, phenyl, methoxy methyl, or triphenylmethyl.

7. The anion exchange porous medium of claim 1, wherein $R^2$ and $R^3$ are H, and $R^5$ and $R^6$ are independently methyl, phenyl, methoxy methyl, or triphenylmethyl.

8. The anion exchange porous medium of claim 1, wherein the crosslinked cationic polymer comprises two different polymerized monomers (A) and one polymerized monomer (B).

9. The anion exchange porous medium of claim 1, wherein the crosslinked cationic polymer comprises two different polymerized monomers (A) and two different polymerized monomers (B).

10. The anion exchange porous medium of claim 1, wherein the crosslinked cationic polymer comprises one polymerized monomer (A) and two different polymerized monomers (B).

11. The anion exchange porous medium of claim 1, which is a membrane.

12. A method for producing an anion exchange porous medium of claim 1, comprising:
- (i) polymerizing a monomer mixture comprising at least one monomer (A) and at least one monomer (B) to obtain a copolymer,
  wherein
  monomer (A) has the formula:
  $$CH_2=C(R^1)-C(=O)-NH-(CH_2)_n-NR^2R^3,$$
  wherein n is 1-6,
  monomer (B) has the formula:
  $$CH_2=C(R^4)-C(=O)-NR^5R^6,$$
  crosslinking the resulting copolymer by reacting with a crosslinking agent having two, three, or more epoxide groups,
  and quaternizing the crosslinked copolymer with a monoglycidyl ether,
  wherein
  $R^1$ and $R^4$ are independently selected from H and $C_1$-$C_6$ alkyl, and
  $R^2$, $R^3$, $R^5$, and $R^6$ are independently selected from the group consisting of H, $C_1$-$C_6$ alkyl, $C_6$-$C_{10}$ aryl, $C_1$-C alkoxy $C_1$-C alkyl, and triphenylmethyl;
- (ii) coating a solution of the copolymer obtained in (i) and a crosslinking agent on a porous support and crosslinking to obtain a crosslinked coating disposed on the porous support; and
- (iii) quaternizing at least a portion of the amino groups present on the copolymer coating obtained in (ii) by reacting with a quaternizing agent selected from the group consisting of isopropyl glycidyl ether, phenyl glycidyl ether, tert-butyl glycidyl ether, ethylhexyl glycidyl ether, glycidyl methyl ether, and benzyl glycidyl ether.

13. The method of claim 12, wherein the crosslinking agent is selected from the group consisting of ethylene glycol diglycidyl ether, propylene glycol diglycidyl ether, glyceryl triglycidyl ether, polyethylene glycol diglycidyl ether, and any combination thereof.

14. A method of treating a fluid containing a protein and one or more negatively charged species, the method comprising contacting the fluid with the anion exchange porous medium of claim 1 and recovering the protein with a reduced concentration of one or more of the negatively charged species.

15. The method of claim 14, wherein the fluid has a salt content such that the fluid exhibits an electrical conductivity of up to 30 mS/cm.

16. The method of claim 14, wherein the protein is an antibody.

17. The method of claim 14, wherein the protein is a biologic.

* * * * *